United States Patent [19]

Antos

[11] 4,141,923

[45] Feb. 27, 1979

[54] DEHYDROCYCLIZATION PROCESS

[75] Inventor: George J. Antos, Arlington Heights, Ill.

[73] Assignee: UOP Inc., Des Plaines, Ill.

[21] Appl. No.: 912,707

[22] Filed: Jun. 5, 1978

Related U.S. Application Data

[63] Continuation-in-part of Ser. No. 803,693, Jun. 6, 1977, Pat. No. 4,101,418, which is a continuation-in-part of Ser. No. 699,748, Jun. 24, 1976, Pat. No. 4,046,711.

[51] Int. Cl.$^2$ .......................... C07C 15/02; B01J 29/12
[52] U.S. Cl. .................................. 260/673.5; 208/139; 252/442; 252/455 Z; 252/466 PT; 260/668 D; 260/673
[58] Field of Search .............................. 260/673, 673.5

[56] References Cited

U.S. PATENT DOCUMENTS

| | | | |
|---|---|---|---|
| 3,642,660 | 2/1972 | Mitsche | 252/442 |
| 3,645,888 | 2/1972 | Hayes | 208/139 X |
| 3,654,184 | 4/1972 | McCallister et al. | 208/139 X |
| 3,759,841 | 9/1973 | Wilhelm | 252/441 |
| 3,772,213 | 11/1973 | Mitsche et al. | 252/466 PT |

*Primary Examiner*—Delbert E. Gantz
*Assistant Examiner*—G. E. Schmitkons
*Attorney, Agent, or Firm*—James R. Hoatson, Jr.; Robert W. Welch; William H. Page, II

[57] ABSTRACT

A process for the catalytic dehydrocyclization of a dehydrocyclizable hydrocarbon is disclosed. The hydrocarbon is passed in contact with a germanium-promoted platinum group metal catalyst at dehydrocyclization reaction conditions, said catalyst having been prepared by impregnating a porous high surface area carrier material with a non-aqueous solution of a platinum group metal compound and a halo-substituted germane containing less than 4 halo substituents and drying and calcining the impregnated carrier material.

21 Claims, No Drawings

DEHYDROCYCLIZATION PROCESS

CROSS-REFERENCE TO RELATED APPLICATIONS

This application is a continuation-in-part of a copending application Ser. No. 803,693 filed June 6, 1977, (now U.S. Pat. No. 4,101,418) which is in turn a continuation-in-part application of a copending application Ser. No. 699,748 filed June 24, 1976, now U.S. Pat. No. 4,046,711.

The present invention relates to a process for the catalytic dehydrocyclization of a dehydrocyclizable hydrocarbon. The process of this invention is particularly useful with respect to the dehydrocyclization of $C_6 - C_8$ paraffinic hydrocarbons to produce the corresponding aromatic hydrocarbons, for example, benzene, toluene, ethylbenzene, and the like. The dehydrocyclization products in return find extensive use, largely as intermediates, in the manufacture of insecticides, detergents, perfumes, drying oils, synthetic fibers, synthetic rubber, pharmaceuticals, and many other articles of commerce.

It is an object of this invention to present an improved catalytic dehydrocyclization process utilizing a dehydrocyclization catalyst comprising a platinum group metal component and a germanium component and characterized by a novel method of preparation.

In one of its broad aspects, the present invention embodies a process for the catalytic dehydrocyclization of a dehydrocyclizable hydrocarbon which comprises passing said dehydrocyclizable hydrocarbon in contact with a germanium-promoted platinum group metal catalyst at dehydrocyclization reaction conditions, said catalyst having been prepared by impregnating a porous high surface area carrier material with a non-aqueous solution of a platinum group metal compound and a halo-substituted germane containing less than 4 halo substituents in an amount to provide a final catalyst containing from about 0.05 to about 1.0 wt. % platinum group metal and from about 0.05 to about 1.0 wt. % germanium, and drying and calcining and reducing the thus impregnated carrier material, said platinum group metal compound being selected from the group consisting of chloroplatinic acid, platinum chloride, ammonium chloroplatinate, dinitrodiaminoplatinum, palladium chloride, chloropalladic acid, rhodium chloride, ruthenium chloride, ruthenium oxide, osmium chloride, chloroiridic acid, and iridium chloride.

One of the more specific embodiments is in a process for the catalytic dehydrocyclization of an aliphatic paraffinic hydrocarbon containing from about 6 to about 20 carbon atoms per molecule which comprises passing said hydrocarbon in contact with a germanium-promoted platinum catalyst in admixture with hydrogen at dehydrocyclization conditions including a temperature of from about 425° to about 595° C., a pressure of from about 0 to about 250 psig., and a hydrogen/hydrocarbon mole ratio of from about 0.1:1 to about 10:1, said catalyst having been prepared by impregnating a porous-high surface area carrier material with a common alcoholic solution of chloroplatinic acid and trichlorogermane in an amount to provide a final catalyst containing from about 0.05 to about 1.0 wt. % platinum and from about 0.05 to about 1.0 wt. % germanium, and drying and calcining and reducing impregnated carrier material.

A still more specific embodiment concerns a process which comprises passing an aliphatic paraffinic hydrocarbon containing from about 6 to about 20 carbon atoms per molecule in contact with a germanium-promoted platinum catalyst in admixture with hydrogen at dehydrocyclization conditions including a temperature of from about 455° to about 535° C., a pressure of from about 50 to about 150 psig., a hydrogen/hydrocarbon mole ratio of from about 0.5:1 to about 5:1, and a substantially water-free environment, said catalyst having been prepared by impregnating a porous high surface area alumina carrier material with a common alcoholic solution of chloroplatinic acid and trichlorogermane in an amount to provide a final catalyst containing from about 0.05 to about 1.0 wt. % platinum and from about 0.05 to about 1.0 wt. % germanium, and drying and calcining and reducing the impregnated alumina at a temperature of from about 425° to about 760° C.

Other objects and embodiments of this invention will become apparent in the following detailed specification.

Hydrocarbons subject to dehydrocyclization in accordance with the process of this invention include the aliphatic paraffinic and aliphatic olefinic hydrocarbons heretofore recognized as susceptible to ring closure and aromatization at dehydrocyclization reaction conditions. Suitable hydrocarbons thus include aliphatic paraffinic hydrocarbons such as n-hexane, 2-methylhexane, 3-methylhexane, 2,2-dimethylhexane, 2,3-dimethylhexane, n-heptane, 2-methylheptane, 3-methylheptane, 4-methylheptane, 2,3-dimethylheptane, 3,4-dimethylheptane, n-octane, 2-methyloctane, 3-methyloctane, 4-methyloctane, 2,3-dimethyloctane, 3,4-dimethyloctane, n-nonane, 2-methylnonane, 3-methylnonane, n-decane, and the like containing from about 6 to about 20 carbon atoms per molecule, and also aliphatic olefinic hydrocarbons such as 1-hexene, 1-heptene, 1-octene, 1-nonene, 1-decene, 1,3-hexadiene, 1,3-heptadiene and the like, containing from about 6 to about 20 carbon atoms per molecule. In a preferred embodiment, aliphatic paraffinic hydrocarbons containing from about 6 to about 10 carbon atoms per molecule are subjected to the dehydrocyclization process of this invention. It is understood that the dehydrocyclizable hydrocarbons can be processed individually, in admixture with other dehydrocyclizable hydrocarbons, or in admixture with other hydrocarbons such as naphthenes, aromatics, $C_1 - C_5$ paraffins, and the like. Thus, mixed hydrocarbon fractions, for example, highly paraffinic straight run naphthas, paraffinic raffinates from aromatic extraction or adsorption, $C_6 - C_{10}$ paraffin-rich streams, etc., commonly available in a typical refinery, are suitable charge stocks. The better results are generally obtained with a charge stock comprising a $C_6 - C_{10}$ paraffinic hydrocarbon mixture, especially a $C_6 - C_{10}$ normal paraffin mixture. The charge stock is most often a paraffin-rich naphtha fraction boiling in the range of from about 60 to about 205° C.

In the preparation of the dehydrocyclization catalyst of this invention, a halo-substituted germane and a platinum group metal compound are prepared in a common non-aqueous solution to deposit a germanium component and a platinum group metal component on a high surface area carrier material. The platinum group metal component is preferably platinum although rhodium, ruthenium, osmium, iridium, and particularly palladium are suitable components. The non-aqueous solution is suitably an absolute alcohol solution, absolute ethanol being preferred. Platinum group metal compounds for use in said non-aqueous solution include chloroplatinic acid, platinum chloride, ammonium chloroplatinate, dinitrodiaminoplatinum, palladium chloride, chloropalladic acid, rhodium chloride, ruthenium chloride, ruthenium oxide, osmium chloride, iridium chloride, chloroiridic acid, and the like. Chloroplatinic acid is a preferred platinum group metal compound for use herein. In any case, the selected platinum group metal compound is utilized in an amount to provide a catalyst product containing from about 0.05 to about 1.0 wt. % platinum group metal.

The halo-substituted germanes herein contemplated are those containing less than four halo-substituents. Preferably, the halo-substituted germane prepared in common solution with the platinum group metal compound is a chlorogermane, i.e., chlorogermane, dichlorogermane or trichlorogermane. Other suitable halo-substituted germanes include the corresponding fluoro-, bromo-, and iodo-substituted germanes, in particular, the normally liquid bromogermane, dibromogermane, tribromogermane and the like. The selected halo-substituted germane is preferably employed in an amount to provide a catalyst product containing from about 0.05 to about 1.0 wt. % germanium. In one preferred embodiment, the halo-substituted germane is trichlorgermane.

The improvement in catalytic activity stability observed in the practice of this invention is believed to result from the formation of a complex of the halo-substituted germane with the platinum group metal compound whereby the germanium and platinum group metal components are deposited and distributed on the surface of the carrier material in intimate association to more fully realize the synergistic potential of said components heretofore observed with respect to the catalytic conversion of hydrocarbons.

Pursuant to the method of the present invention, a high surface area, porous carrier material is impregnated with the described non-aqueous impregnating solution. Suitable carrier materials include any of the various and wellknown solid adsorbent materials generally utilized as a catalyst support or carrier material. Said adsorbent materials include the various charcoals produced by the destructive distillation of wood, peat, lignite, nutshells, bones, and other carbonaceous matter and preferably such charcoals as have been heat treated, or chemically treated, or both, to form a highly porous particle structure of increased adsorbent capacity, and generally defined as activated carbon. Said adsorbent materials also include the naturally occurring clays and silicates, for example, diatomaceous earth, fuller's earth, kieselguhr, attapulgus clay, feldspar, montmorillonite, halloysite, kaolin and the like, and also the naturally occurring or synthetically prepared refractory inorganic oxides such as alumina, silica, zirconia, thoria, boria, etc., or combinations thereof like silica-alumina, silica-zirconia, alumina-zirconia, etc. The preferred porous carrier materials for use in the present invention are the refractory inorganic oxides with best results being obtained with an alumina carrier material. It is preferred to employ a porous, adsorptive, high surface area material characterized by a surface area of from about 25 to about 500 m$^2$/gm. Suitable aluminas thus include gamma-alumina, eta-alumina, and thetaalumina, with the first mentioned gamma-alumina being preferred. A particularly preferred alumina is gamma-alumina characterized by an apparent bulk density of from about 0.30 to about 0.90 gms. per cc, an average pore diameter of from about 50 to about 150 Angstroms, an average pore volume of from about 0.10 to about 1.0 cc/gm., and a surface area of from about 150 to about 500 m$^2$/gm.

The alumina employed may be a naturally occurring alumina or it may be synthetically prepared in any conventional or otherwise convenient manner. The alumina is typically employed in a shape or form determinative of the shape or form of the final catalyst composition, e.g., spheres, pills, granules, extrudates, powder, etc. A particularly preferred form of alumina is the sphere, especially alumina spheres prepared substantially in accordance with the oil-drop method described in U.S. Pat. No. 2,620,314. Briefly, said method comprises dispersing droplets of an alumina sol in a hot oil bath. The droplets are retained in the oil bath until they set into firm gel spheroids. The spheroids are continuously separated from the bath and subjected to specific aging treatments to promote certain desirable properties. The spheres are subsequently dried at from about 40° to about 200° C. and thereafter calcined at from about 4250° to about 760° C.

Impregnating conditions employed herein involve conventional impregnating techniques known to the art. Thus, the catalytic component, or soluble compound thereof, is adsorbed on the carrier material by soaking, dipping, suspending, or otherwise immersing the carrier material in the impregnating solution, suitably at ambient temperature conditions. The carrier material is preferably maintained in contact with the impregnating solution at ambient temperature conditions for a brief period, preferably for at least about 30 minutes, and the impregnating solution thereafter evaporated substantially to dryness at an elevated temperature. For example, a volume of alumina particles is immersed in a substantially equal volume of impregnating solution in a steam-jacketed rotary dryer and tumbled therein for a brief period at about room temperature. Thereafter, steam is applied to the jacket of the dryer to expedite the evaporation of said solution and recovery of substantially dry impregnated carrier material.

Catalysts such as herein contemplated typically are prepared to contain a halogen component which may be chlorine, fluorine, bromine and/or iodine. The halogen component is generally recognized as existing in a combined form resulting from physical and/or chemical combination with the carrier or other catalyst components. While at least a portion of the halogen components may be incorporated in the catalyst composition during preparation of the carrier material, sufficient halogen is contained in the aforesaid impregnating solution to enhance to acidic function of the catalyst product in the traditional manner. In any case, a final adjustment of the halogen level may be made in the manner hereinafter described.

Regardless of the details of how the components of the catalyst are combined with the porous carrier material, the final catalyst composite generally will be calcined in an oxidizing atmosphere, such as air, at a temperature of from about 200° to about 650° C. The catalyst particles are advantageously calcined in stages to experience a minimum of breakage. Thus, the catalyst particles are advantageously calcined for a period of from about 1 to about 3 hours in an air atmosphere at a temperature of from about 200° to about 375° C., and immediately thereafter at a temperature of from about 475° to about 650° C. in an air atmosphere for a period of from about 3 to about 5 hours. Best results are generally obtained when the halogen content of the catalyst is adjusted during the calcination step by including a halogen or a halogen-containing compound in the air atmosphere utilized. In particular, when the halogen component of the catalyst is chlorine, it is preferred to use a mole ratio of $H_2O$ to HCl of from about 20:1 to about 100:1 during at least a portion of the calcination step in order to adjust the final chlorine content of the catalyst to a range of from about 0.6 to about 1.2 wt. %.

It is preferred that the resultant calcined catalytic composite is subjected to a substantially water-free reduction step prior to its use in the conversion of hydrocarbons. This step is designed to further insure a uniform and finely divided dispersion of the metallic components throughout the carrier material. Preferably, substantially pure and dry hydrogen (i.e., less than 20 vol. ppm. $H_2$) is used as the reducing agent in this step. The reducing agent is contacted with the oxidized catalyst at conditions including a temperature of from about 425° to about 675° C. This reduction step may be performed in situ as part of a start-up sequence if precautions are taken to predry the plant to a substantially water-free state and if substantially water-free hydrogen is used. The duration of this step is preferably less than 2 hours, and more typically about 1 hour.

The dehydrocyclizable hydrocarbon is generally passed in contact with the described catalyst in admixture with hydrogen to suppress the formation of hydrogen-deficient carbonaceous matter on the catalyst and to lower the partial pressure of the dehydrocyclizable hydrocarbon. Sufficient hydrogen is charged to provide a hydrogen/hydrocarbon mole ratio of from about 0.1:1 to about 10:1, and preferably from about 0.5:1 to about 5:1. Further, the dehydrocyclization reaction is advantageously effected in a substantially waterfree environment, and this is promoted by a careful control of the water level of the hydrocarbon and hydrogen feed stock. This can be effected by passing the feed stock over a solid adsorbent such as silica gel, activated alumina, anhydrous calcium sulfate, high surface area sodium, and the like, to reduce the water level to less than about 20 ppm., and preferably less than about 5 ppm.

Dehydrocyclization reaction condition further include a pressure of from about 0 to about 250 psig. and a temperature of from about 425° to about 595° C. Preferably, dehydrocyclization of the dehydrocyclizable hydrocarbons in contact with the catalyst of this invention is effected at a pressure of from about 50 to about 150 psig. and at a temperature of from about 455° to about 535° C. The dehydrocyclizable hydrocarbon is suitably maintained in contact with the described catalyst for a time equivalent to a liquid hourly space velocity of from about 0.1 to about 5, and preferably a liquid hourly space velocity of from about 0.3 to about 2.

The following example is presented in illustration of one preferred embodiment of this invention and is not intended as an undue limitation on the generally broad scope of the invention as set out in the appended claims.

EXAMPLE I

Gamma-alumina spheres of about 1/16" diameter were prepared by the described oil-drop method. Thus, an aluminum chloride hydrosol, prepared by digesting aluminum pellets in dilute hydrochloric acid, was commingled with hexamethylenetetramine and dispersed as droplets in a hot oil bath. The resulting spheres were aged in the oil bath overnight and then washed, dried and calcined. The alumina spheres had an average bulk density of about 0.5 gms/cc and a surface area of about 180 $m^2$/gms.

In preparing the impregnating solution, trichlorogermane and chloroplatinic acid were dissolved in absolute ethanol to form a common solution thereof. The solution was stabilized with a quantity of HCl equivalent to about 3 wt. % of the alumina to be impregnated. The solution was thereafter diluted to about 350cc.

About 350cc of the calcined alumina spheres were immersed in the impregnating solution in a steam-jacketed rotary evaporator, the volume of the impregnating solution being substantially equivalent to the volume of the carrier material. The spheres were allowed to soak in the rotating evaporator for about 30 minutes at room temperature and steam was thereafter applied to the evaporator jacket. The solution was evaporated substantially to dryness, and the dried spheres were subsequently dried in air for about 1 hour at 150° C. and immediately thereafter calcined in air for about 2 hours at 525° C. The catalyst particles were then treated in a substantially pure hydrogen stream containing less than about 20 vol. ppm. $H_2O$ for about 1 hour at 565° C. to yield the reduced form of the catalyst. The final catalyst product contained 0.375 wt. % platinum and 0.25 wt. % germanium calculated as the elemental metal.

In a continuous process for the dehydrocyclization of n-hexane representing one preferred embodiment of this invention, the described catalyst is disclosed as a fixed bed in a vertical tubular reactor equipped with a preheater and suitable heating means whereby the reactant stream is preheated to about 525° C. and maintained at about this temperature in contact with the catalyst bed. A commercial grade of n-hexane is charged to the reactor by means of a compressor at a rate to effect a liquid hourly space velocity of about 0.75. The n-hexane is admixed with a hydrogen-rich recycled gas to effect a recycled gas/hydrocarbon mole ratio of about 4:1, and the mixture is processed downwardly through the catalyst bed at said liquid hourly space velocity of about 0.75. The reactor outlet pressure is controlled at about 125 psig. The reactor effluent stream is passed to a high pressure-low temperature separator wherein the reactor effluent is cooled to a temperature of about 13° C. and separated into a liquid phase and a gaseous phase. A portion of the hydrogenrich gaseous phase is continuously withdrawn from the separator and recycled to provide the aforementioned recycle gas/hydrocarbon mole ratio charged to the reactor. The liquid phase is continuously withdrawn from the separator through a pressure reducing valve and charged to a distillation column wherein a $C_5-$ product is distilled overhead. The bottoms fraction comprises about 40 wt. % dehydrocyclization product, about one-half of which is benzene for an overall selectivity to benzene of about 25%.

I claim as my invention:
1. A process for the catalytic dehydrocyclization of a dehydrocyclizable hydrocarbon which comprises passing and hydrocarbon in contact with a germanium-promoted platinum group metal catalyst at dehydrocyclization reaction conditions, said catalyst having been prepared by impregnating a porous high surface area carrier material with a non-aqueous solution of a platinum group metal compound and a halo-substituted germane containing less than 4 halo substituents in an amount to provide a final catalyst containing from about 0.05 to about 1.0 wt. % platinum group metal and from about 0.05 to about 1.0 wt. % germanium, and drying and calcining the thus impregnated carrier material, said platinum group metal compound being selected from the group consisting of chloroplatinic acid, platinum chloride, ammonium chloroplatinate, dinitrodiaminoplatinum, palladium, chloride, chlorpalladic acid, rhodium chloride, ruthenium chloride, ruthenium oxide, osmium chloride and iridium chloride.

2. The process of claim 1 further characterized in that said soluble platinum group metal compound is a platinum compound.

3. The process of claim 1 further characterized in that said soluble platinum group metal compound is chloroplatinic acid.

4. The process of claim 1 further characterized in that said halo-substituted germane is a chloro-substituted germane.

5. The process of claim 1 further characterized in that said halo-substituted germane is trichlorogermane.

6. The process of claim 1 further characterized in that said non-aqueous solution is an alcoholic solution.

7. The process of claim 1 further characterized in that said carrier material is a refractory inorganic oxide.

8. The process of claim 1 further characterized in that said carrier material is an alumina carrier material.

9. The process of claim 1 further characterized in that said impregnated carrier material is dried and calcined at a temperature of from about 425° to about 760° C.

10. The process of claim 1 further characterized in that said dehydrocyclizable hydrocarbon is passed in contact with said catalyst in admixture with hydrogen.

11. The process of claim 1 further characterized in that said dehydrocyclizable hydrocarbon is passed in contact with said catalyst in a substantially water-free environment.

12. The process of claim 1 further characterized in that said dehydrocyclization conditions include a temperature of from about 425° to about 595° C., a pressure of from about 0 to about 250 psig., and a hydrogen/hydrocarbon mole ratio of from about 0.1:1 to about 10:1.

13. The process of claim 1 further characterized in that said dehyrocyclization conditions include a temperature of from about 455° to about 535° C., a pressure of from about 50 to about 150 psig., and a hydrogen/hydrocarbon mole ratio of from about 0.5:1 to about 5:1.

14. The process of claim 1 further characterized in that said dehydrocyclizable hydrocarbon is an aliphatic hydrocarbon containing from about 6 to about 20 carbon atoms per molecule.

15. The process of claim 1 further characterized in that said dehydrocyclizable hydrocarbon is an olefinic aliphatic hydrocarbon containing from about 6 to about 20 carbon atoms per molecule.

16. The process of claim 1 further characterized in that said dehydrocyclizable hydrocarbon is a paraffinic aliphatic hydrocarbon containing from about 6 to about 20 carbon atoms per molecule.

17. The process of claim 1 further characterized in that said dehydrocyclizable hydrocarbon is hexane.

18. The process of claim 1 further characterized in that said dehydrocyclizable hydrocarbon is heptane.

19. The process of claim 1 further characterized in that said dehydrocyclizable hydrocarbon is octane.

20. The process of claim 1 further characterized in that said dehydrocyclizable hydrocarbon is nonane.

21. The process of claim 1 further chracterized in that said dehydrocyclizable hydrocarbon is contained in a naphtha fraction boiling in the range of from about 60° to about 205°0 C.

* * * * *